United States Patent [19]

Serafini et al.

[11] Patent Number: 4,900,859

[45] Date of Patent: Feb. 13, 1990

[54] PROCESS FOR 4-DIMETHYLAMINO-3,5-DIMETHOXYBEN-ZALDEHYDE

[75] Inventors: Siro Serafini, Vicenza; Giuseppe Zagotto, Terrossa, both of Italy

[73] Assignee: Hoffman-La Roche Inc., Nutley, N.J.

[21] Appl. No.: 272,366

[22] Filed: Nov. 17, 1988

[30] Foreign Application Priority Data

Dec. 3, 1987 [CH] Switzerland .................. 4721/87

[51] Int. Cl.$^4$ ............... C07B 41/06; C07C 121/52
[52] U.S. Cl. ................................. 558/418; 564/305
[58] Field of Search .................. 558/418; 564/305

[56] References Cited

U.S. PATENT DOCUMENTS

| | | | |
|---|---|---|---|
| 3,933,887 | 1/1976 | Gengnagel | 558/418 |
| 3,971,821 | 7/1976 | Baumann et al. | 558/418 |
| 4,273,785 | 6/1981 | Shepherd | 564/305 |
| 4,440,950 | 4/1984 | Drake | 564/305 |
| 4,515,948 | 5/1985 | Kompis et al. | 544/325 |

FOREIGN PATENT DOCUMENTS

| | | |
|---|---|---|
| 0280975 | 9/1988 | European Pat. Off. |
| 1022741 | 3/1966 | United Kingdom ........ 564/305 |

*Primary Examiner*—Joseph Paul Brust
*Assistant Examiner*—MarySue Howard
*Attorney, Agent, or Firm*—George M. Gould; Bernard S. Leon; William G. Isgro

[57] ABSTRACT

4-Dimethylamino-3,5-dimethoxy-benzaldehyde, an intermediate for the preparation of the antibacterially active aditoprim (4-dimethylamino-3,5-dimethoxybenzoldehyde) a known antibacterially active compound, is obtained from 4-dimethylaminobenzonitrile by bromination or chlorination, replacement of the halogen by the methoxy group and reduction of the nitrile group.

6 Claims, No Drawings

PROCESS FOR 4-DIMETHYLAMINO-3,5-DIMETHOXYBENZALDEHYDE

BRIEF SUMMARY OF THE INVENTION

The invention relates to a process for the preparation of 4-dimethylamino-3,5-dimethoxybenzaldehyde which comprises the steps of:

(a) converting 4-dimethylaminobenzonitrile into 3,5-dibromo-(or dichloro-)4-methylaminobenzonitrile by treatment with bromine or chlorine;

(b) converting the resulting 3,5-dibromo-(or dichloro-)-4-methylaminobenzonitrile into 3,5-dimethoxy-4-methylaminobenzonitrile by treatment with alkali methoxide in the presence of copper and dimethylformamide or dimethylacetamide; and (c) methylating 3,5-dimethoxy-4-methylaminobenzonitrile to 4-dimethylamino-3,5-dimethoxybenzonitrile and reducing the latter to 4-dimethylamino-3,5-dimethoxybenzaldehyde.

DETAILED DESCRIPTION OF THE INVENTION

The invention relates to a process for the preparation of 4-dimethylamino-3,5-dimethoxybenzaldehyde and with intermediates which occur in this process, namely, 3,5-dibromo-(and 3,5-dichloro-)4-methylaminobenzonitrile as well as 3,5-dimethoxy-4-methylaminobenzonitrile.

4-Dimethylamino-3,5-dimethoxybenzaldehyde is an intermediate utilized in the preparation of 2,4-diamino-5-(3,5-dimethoxy-4-dimethylamino)benzylpyrimidine (aditoprim), an antibacterially active compound.

For the economical utilization of aditoprim, especially in the field of veterinary medicine, the high manufacturing costs for this compound have hitherto been an obstacle when known manufacturing processes, for example, the process described in DE Patent Specification No. 2 443 682, had to be employed.

The process of the invention enables aditoprim to be prepared with substantially more economical costs than has been possible with the known processes. This result is achieved by making 4-dimethylamino-3,5-dimethoxybenzaldehyde available with more favorable costs by the reaction sequence employed in the process of the invention. Aditoprim can be prepared from this aldehyde in a known manner. The process in accordance with the invention is characterized by (a) converting 4-dimethylaminobenzonitrile into 3,5-dibromo-(or dichloro-)4-methylaminobenzonitrile by treatment with bromine or chlorine;

(b) converting the resulting 3,5-dibromo-(or dichloro-)-4-methylaminobenzonitrile into 3,5-dimethoxy-4-methylaminobenzonitrile by treatment with alkali methoxide in the presence of copper and dimethylformamide or dimethylacetamide; and (c) methylating 3,5-dimethoxy-4-methylaminobenzonitrile to 4-dimethylamino-3,5-dimethoxybenzonitrile and reducing the latter to 4-dimethylamino-3,5-dimethoxybenzaldehyde.

In a preferred embodiment of process step (a), the halogenating agent, for example, bromine, is produced in situ from an aqueous hydrohalic acid and an oxidizing agent, preferably, hydrogen peroxide. The halogenation is conveniently carried out at temperatures in a range of between room temperature and about 60° C., especially at about 40°–50° C. The reaction can be carried out in any inert organic solvent. Methanol is a preferred solvent. The thus-obtained 3,5-dibromo-(or 3,5-dichloro)-4-methylaminobenzonitrile can be separated in solid form by cooling the reaction mixture.

Sodium methoxide is conveniently used as the alkali methoxide in process step (b). Methanol preferably comes into consideration as the solvent. The dimethylformamide or the dimethylacetamide utilized has the function of a N-acylating agent. The intermediately-formed N-formyl or N-acetyl group is cleaved off in the basic medium in the course of the working-up of the reaction mixture. The amount of this intermediately-active N-acylating agent conveniently amounts to about 2–10 equivalents. Copper can be used as the powdery metal or, preferably, as a Cu(I) compound such as $Cu_2O$ or Cu(I) halide, especially CuCl. The reaction is conveniently carried out while heating, preferably, at the reflux temperature of the reaction mixture. The reaction product can be separated from the reaction mixture by usual working-up, for example, by extraction.

In process step (c), the process product obtained in (b), conveniently, as the crude product without further purification, is first reacted with a methylating agent, preferably, with formaldehyde/formic acid according to Eschweiler-Clarke. The methylation product is then treated with a reducing agent which is suitable for the conversion of a nitrile group into an aldehyde group. Raney-nickel alloy, (a Ni-Al alloy), is a suitable reagent for this reduction. The reduction can be carried out by adding the reducing agent to the reaction mixture containing the methylation product, 4-dimethylamino-3,5-dimethoxybenzonitrile. The reduction product, 4-dimethylamino-3,5-dimethoxybenzaldehyde, can be separated from the reaction mixture by usual working-up, for example, extraction with an organic solvent such as toluene. The thus-obtained crude product can be converted directly, for example, without further purification, into aditoprim in a known manner.

The following Examples further illustrate the invention. Temperatures are in degrees Centigrade, unless otherwise stated.

EXAMPLE 1

Preparation of 3,5-dibromo-4-methylaminobenzonitrile 105 g of 4-dimethylaminobenzonitrile are dissolved in 560 ml of methanol. The solution is treated at about 40° C. while stirring with 366 g of 60% aqueous hydrobromic acid. Thereafter, 198 g of 35% hydrogen peroxide are added in the course of 45 minutes, whereby the temperature is held at 50° C. The mixture is stirred at 50° C. for an additional 4 hours, then cooled to 15°–20° C. and filtered. The filter cake is washed neutral with water, dried, and 153 g of 3,5-dibromo-4-methylaminobenzonitrile are obtained.

EXAMPLE 2

Preparation of 3,5-dimethoxy-4-methylaminobenzonitrile 167 g of sodium methoxide are dissolved in 460 ml of methanol while stirring and cooling. Thereafter, 25 g of copper(I) chloride and 153 g of 3,5-dibromo-4-methylaminobenzonitrile as well as 76 ml of dimethylformamide are added. The mixture is heated to reflux for 4.5 hours, cooled to 25°–30° C. and treated with 450 ml of toluene, 450 ml of water and 7.5 g of active charcoal. The mixture is filtered and the organic phase is washed with a solution of 160 ml of water and 16 ml of acetic acid (pH about 6). The organic phase is separated and concentrated under reduced pressure, whereby there are obtained about 91 g of 3,5-dimethoxy-4-methylaminobenzonitrile in the form of an oily residue which crystallizes upon standing and which is used in this form in the next reaction step.

EXAMPLE 3

Preparation of 4-dimethylamino-3,5-dimethoxybenzaldehyde

A mixture of 91 g of the 3,5-dimethoxy-4-methylaminobenzonitrile obtained in Example 2, 726 g of formic acid and 29 g of p-formaldehyde are heated to reflux for 1 hour. The mixture is then cooled to 20°–30° C. and treated with 181 ml of water and 91 g of Raney-nickel alloy. The reaction mixture is heated to reflux for 1.5 hours, whereby the reaction starts vigorously at 80° C. The reaction mixture is cooled to 25°–30° C. and filtered in such a manner that the metal is always covered with solvent. The filter cake is washed with formic acid and the solution is evaporated under reduced pressure and thereafter treated with 360 ml of toluene and 360 ml of water. The pH is adjusted to 5.5 to 6 by adding 30% aqueous sodium hydroxide solution. After adding 7 g of active charcoal, the reaction mixture is filtered. The filter cake is washed with toluene and the organic phase is concentrated under reduced pressure.

80 g of 4-dimethylamino-3,5-dimethoxybenzaldehyde are obtained as an oil.

We claim:
1. A process for the preparation of 4-dimethylamino-3,5-dimethoxybenzaldehyde, which comprises:
    (a) converting 4-dimethylaminobenzonitrile into 3,5-dibromo-(or dichloro-)4-methylaminobenzonitrile by treatment with bromine or chlorine;
    (b) converting 3,5-dibromo-(or dichloro-)-4-methylaminobenzonitrile, the reaction product of step (a) into 3,5-dimethoxy-4-methylaminobenzonitrile by treating said reaction product with an alkali methoxide in the presence of copper and dimethylformamide or dimethylacetamide; and
    (c) methylating 3,5-dimethoxy-4-methylaminobenzonitrile, the reaction product of step (b) to 4-dimethylamino-3,5-dimethoxybenzonitrile and reducing the latter to 4-dimethylamino-3,5-dimethoxybenzaldehyde.
2. A process according to claim 1, wherein a Cu(I) compound is used in step (b).
3. A process according to claim 1, wherein the reduction in step (c) is carried out by Raney-Ni alloy.
4. A compound of the formula 3,5-dibromo-4-methylaminobenzonitrile.
5. A compound of the formula 3,5-dichloro-4-methylaminobenzonitrile
6. A compound of the formula 3,5-dimethoxy-4-methylaminobenzonitrile.

* * * * *